(12) United States Patent
Kundscher et al.

(10) Patent No.: US 9,335,197 B2
(45) Date of Patent: May 10, 2016

(54) RETRACTABLE ASSEMBLY

(71) Applicant: Endress + Hauser Conducta Gesellschaft für Mess- und Regeltechnik mbH + Co. KG, Gerlingen (DE)

(72) Inventors: Rene Kundscher, Waldheim (DE); Thomas Pfauch, Leipzig (DE); Andre Pfeifer, Schkopau (DE)

(73) Assignee: ENDRESS & HAUSER CONDUCTA GESELLSCHAFT FÜR MESS-UND REGELTECHNIK MBH+ CO. KG, Gerlingen (DE)

( * ) Notice: Subject to any disclaimer, the term of this patent is extended or adjusted under 35 U.S.C. 154(b) by 180 days.

(21) Appl. No.: 13/875,455

(22) Filed: May 2, 2013

(65) Prior Publication Data

US 2013/0291633 A1 Nov. 7, 2013

(30) Foreign Application Priority Data

May 3, 2012 (DE) .......................... 10 2012 103 874

(51) Int. Cl.
*G01F 15/14* (2006.01)
*G01F 15/18* (2006.01)
(Continued)

(52) U.S. Cl.
CPC .............. *G01F 15/14* (2013.01); *G01F 15/185* (2013.01); *G01F 23/00* (2013.01); *G01F 3/12* (2013.01)

(58) Field of Classification Search
CPC ............ G01F 15/14; G01F 3/12; G01F 15/18
USPC ........................ 73/273, 272, 866.5; 422/82.01
See application file for complete search history.

(56) References Cited

U.S. PATENT DOCUMENTS

| 3,186,163 | A * | 6/1965 | Dixon .............................. 60/636 |
| 7,272,983 | B2 | 9/2007 | Caderas |
| 7,594,449 | B2 | 9/2009 | Tottewitz et al. |

(Continued)

FOREIGN PATENT DOCUMENTS

| DE | 29720248 U1 * | 3/1998 |
| DE | 102 41 833 A1 | 3/2004 |

(Continued)

OTHER PUBLICATIONS

German Search Report dated Apr. 8, 2013, issued in Application 10 2012 103 874.0, in Munich, Germany.

*Primary Examiner* — Lisa Caputo
*Assistant Examiner* — Nathaniel T Woodward
(74) *Attorney, Agent, or Firm* — Bacon & Thomas, PLLC

(57) ABSTRACT

A retractable assembly, comprising: a housing; an immersion tube, which is axially movable between a service position and a process position. A first inlet facing away from the medium and a second inlet facing the medium. The immersion tube is moved from the service position to the process position by supplying the first inlet with energy, and the immersion tube is moved from the process position to the service position by supplying the second inlet with energy. A first mechanical blocking member shifts against a spring bias, and the blocking member engages in a first groove on the immersion tube. The first groove is located in the movement direction. The spring bias is so embodied that supplying the second inlet with energy releases the blocking member from the groove, whereby movement of the immersion tube from process position to service position becomes possible.

12 Claims, 3 Drawing Sheets

(51) Int. Cl.
*G01F 23/00* (2006.01)
*G01F 3/12* (2006.01)

(56) References Cited

U.S. PATENT DOCUMENTS

2008/0250948 A1* 10/2008 Aoki et al. .................... 100/282
2009/0214387 A1* 8/2009 Straub et al. ............... 422/82.01
2013/0036843 A1 2/2013 Pfauch et al.

FOREIGN PATENT DOCUMENTS

| | | |
|---|---|---|
| DE | 10 2010 001 876 A1 | 8/2011 |
| DE | 20 2012 002 473 U1 | 7/2012 |
| DE | 10 2011 079 348 A1 | 1/2013 |
| DE | 10 2011 080 579 A1 | 2/2013 |
| EP | 0 882 896 B1 | 12/1998 |
| EP | 1 752 763 | 2/2007 |

* cited by examiner

RETRACTABLE ASSEMBLY

TECHNICAL FIELD

The invention relates to a retractable assembly for immersion-, flow- and annex-measuring systems especially in analytical process technology for measuring at least one measured variable of a medium.

BACKGROUND DISCUSSION

Retractable assemblies are widely used in analytical measurements technology. They serve for introducing and removing probes to and from a process and its media without process interruption. The probes are secured in an immersion tube and, by means of a drive, moved manually or automatically, for example, pneumatically, axially between a process position and a service position. These events happen within a certain timing cycle or as a function of other determinable or measured parameters.

Probes in the sense of this invention comprise probes with at least one accommodation for at least one sensor for measuring one or more physical or chemical, process variables.

The fields of use of retractable assemblies for measuring physical or chemical, process variables of a medium, e.g. a fluid, especially a liquid, in process technology are many. Sensors are used for determining the process variables, wherein the sensors can be, for example, pH-sensors, conductivity sensors, optical or electrochemical sensors for determining a concentration of a substance contained in the medium to be monitored, e.g. $O_2$, $CO_2$, certain types of ions, organic compounds, etc.

If retractable assemblies are used for accommodating a sensor for determining at least one process variable, the sensor can be checked, calibrated, cleaned and/or replaced in the service position, wherein the sensor is located, in such case, in a treatment chamber arranged in the housing of the retractable assembly.

Retractable assemblies are available from the group of firms, Endress+Hauser, in a large multiplicity of variants, one example being that bearing the designation, "Cleanfit H CPA475".

Frequently, high temperatures and, especially, high pressures reign in a process. A process pressure of 10 bar and more is no rarity. If the immersion tube is in the process run-in position (process position), this pressure acts then also on the immersion tube, and the immersion tube has the tendency to be pressed back into the assembly. This must be prevented, since, otherwise—in the simplest case—the measuring can be corrupted/prevented, or—in the worst case—safety of the operating personnel or the environment can be endangered when process medium escapes without control. As long as the drive is working correctly, there is no problem. If, however, for some reason, the drive is no longer capable of functioning, the immersion tube can be pushed by the process pressure back into the assembly and therewith into an undefined position.

Equally, such reasoning holds for the opposite case, namely, when the immersion tube is located in the service position, an uncontrolled drawing of the immersion tube into the process must be prevented.

Known from the state of the art (compare the mentioned CPA475) are manually locking bolts, which lessen the degree of automation, and, in the case of improper handling, represent a significant safety risk.

European Patent EP 0545 177 A1 shows a safety system for an immersion tube, wherein its shiftability from the process position is blocked when the drive becomes non-functional. However, in the case of intact drive, the immersion tube can still be manually pushed into the process or drawn from the process. Moreover, additional lines/hoses are needed for the safety system.

SUMMARY OF THE INVENTION

An object of the invention is, consequently, to provide a safety system, which assures in any situation that the immersion tube cannot move uncontrollably from the service, respectively process, position.

The object is achieved by a retractable assembly, comprising: an essentially cylindrical housing; an immersion tube with a piston, wherein the immersion tube is axially movable between a service position run out from the medium and a process position run into the medium by means of an energy supply, especially pressurized air, wherein at least a first inlet and a second inlet are provided on the housing, wherein the first inlet is located on the side of the piston facing away from the medium and the second inlet on the side of the piston facing the medium, wherein the immersion tube is moved from service position to process position by supplying the first inlet with energy, and wherein the immersion tube is moved from process position to service position by supplying the second inlet with energy; at least a first end position detent secured to the housing for holding the immersion tube in the process position, wherein, at an immersion tube end region facing the medium, a first shifting element is provided, which is so embodied that, in the case of moving of the immersion tube from service position to process position, a first mechanical blocking member shifts essentially radially against a spring bias, and the blocking member engages in a first groove on the immersion tube, whereby movability of the immersion tube is blocked, wherein the first groove is located in the movement direction from service position to process position behind the first mechanical blocking member, and wherein the spring bias is so embodied that supplying of the second inlet with energy releases the blocking member from the groove, whereby movement of the immersion tube from process position to service position becomes possible.

The shifting element shifts automatically, through movement of the immersion tube from service to process position, a blocking member, which, in the course of further movement of the immersion tube, engages in a groove on the immersion tube and, thus, prevents further movement of the immersion tube. The shifting of the immersion tube from service to process position also expels pressurized air by means of the piston through the second inlet. This pressurized air can also shift the blocking member against the spring and thus the piston can pass the blocking member unimpeded. Then, the blocking member engages in the groove provided therefor.

The mechanical blocking member thus prevents an uncontrolled movement of the immersion tube independently of the drive and the presence of pressurized air, i.e., in the case of failure of the drive, the immersion tube is safely locked. Only in the case of intended supplying of the second, process-facing inlet with pressurized air is a rearwards movement possible. In such case, first the blocking member is released from the groove against the spring bias, and then the immersion tube can move back from process to service position. All present lines can be used and no additional lines are necessary.

Thus, the object of the invention is achieved. The immersion tube can neither in the case of failure of the drive nor improperly by hand be pushed into an undefined position, but, instead, remains in the service or the process position, as the case may be.

In an embodiment, supplementally a second end position detent is provided secured to the housing for holding the immersion tube in the service position, wherein, at an immersion tube end region facing away from the medium, a second shifting element is provided, which is so embodied that, in the case of moving of the immersion tube from process position to service position, a second mechanical blocking member shifts essentially radially against a spring bias, and the blocking member engages in a second groove on the immersion tube, whereby movability of the immersion tube is blocked, wherein the second groove is located in the movement direction from process position to service position behind the second mechanical blocking member, and wherein the spring bias is so embodied that supplying of the first inlet with energy releases the blocking member from the groove, whereby movement of the immersion tube from service position to process position becomes possible.

The shifting element shifts automatically, through movement of the immersion tube from process to service position, a blocking member, which, in the course of further movement of the immersion tube, engages in a groove on the immersion tube and, thus, prevents movement of the immersion tube. The shifting of the immersion tube from process to service position also expels pressurized air by means of the piston through the first inlet. This pressurized air can also shift the blocking member against the spring bias, so that the piston can pass by the blocking member unimpeded. Then, the blocking member engages in the groove provided therefor.

The mechanical blocking member thus prevents an uncontrolled movement of the immersion tube independently of the drive and presence of pressurized air, i.e. in the case of failure of the drive, the immersion tube is safely locked. Only in the case of intentional supplying of the first inlet facing away from the process with pressurized air is movement again possible. In such case, first, the blocking member is released from the groove by its shifting counter to the spring bias, and then the immersion tube can move back from service to process position.

In a form of embodiment, the shifting element is conically embodied, wherein the base of the cone is located on the immersion tube. In a variant, in such case, the shifting element is embodied as a frustum. In a special embodiment, the frustum is embodied by a securement element with conical head. In an advantageous further development, the half cone angle of the cone shaped shifting element amounts to less than/equal to 45°. These special forms of embodiment assure that the shifting element can radially shift the blocking member essentially as simply and friction freely as possible and no (great) additional energy is necessary therefor.

Advantageously, at least one of the grooves is embodied as an annular groove. This can be manufactured relatively simply and enabled an optimal securement of the locking element, respectively the immersion tube.

In a preferred variant, a sliding ring is provided in the at least one groove for increasing the movability of the immersion tube, wherein a region of the sliding ring is omitted for the blocking member.

Alternatively to the annular groove, at least one of the grooves is embodied as a circular segment shaped groove, radial bore or as a tangential cavity on the periphery of the immersion tube.

It can occur, for example, for safety reasons, that the immersion tube must be quickly released from the locked position. Therefore, an emergency unlock is provided, which releases the blocking member from the groove and so enables movement of the immersion tube even when no energy supply is present.

BRIEF DESCRIPTION OF THE DRAWINGS

The invention will now be explained in greater detail based on the appended drawing, the figures of which show as follows.

DETAILED DISCUSSION IN CONJUNCTION WITH THE DRAWINGS

Figure 1:
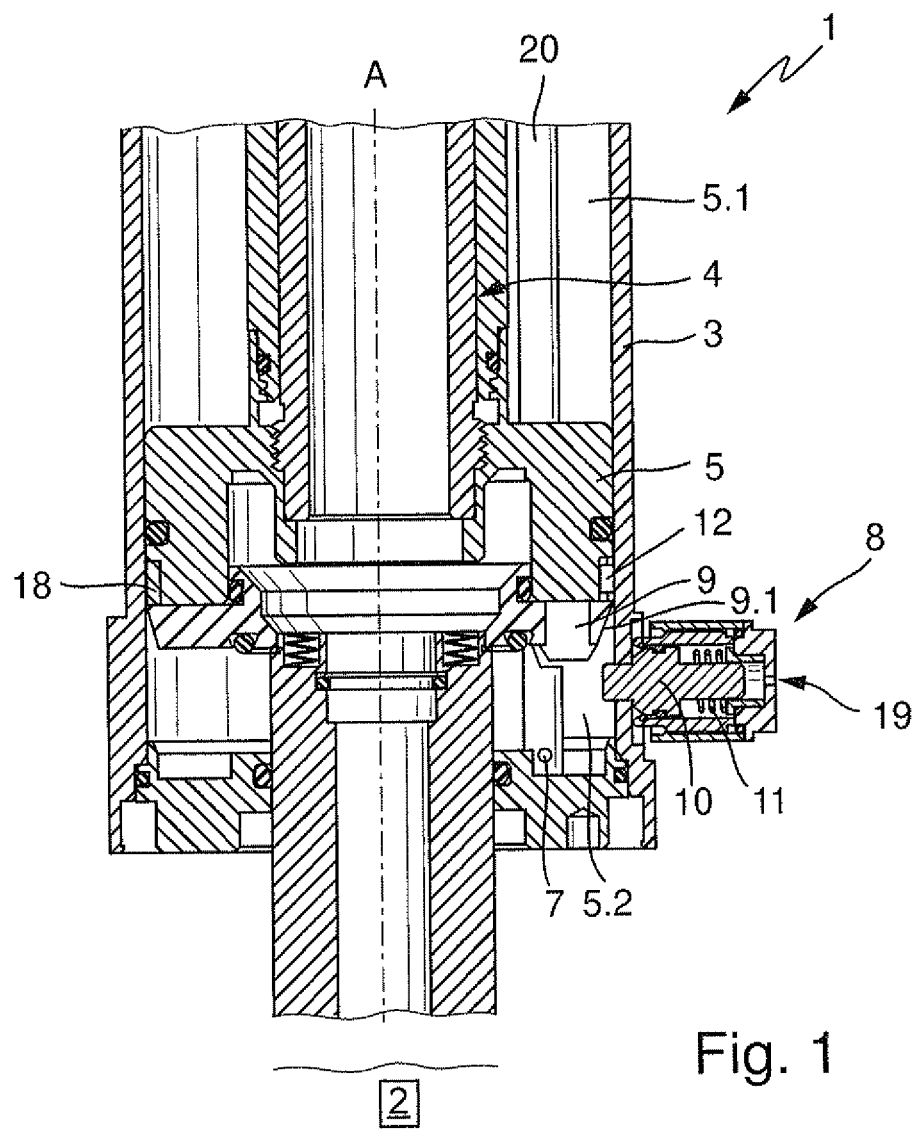
FIG. 1 a cross section of the retractable assembly of the invention shortly before the immersion tube reaches the process position.

In the figures, equal features are provided with equal reference characters.

The retractable assembly of the invention in its totality is given the reference character 1. Retractable assembly 1 is composed of an essentially cylindrical housing 3, which can be connected to a containment by means of a connection not shown in greater detail. This can be, for example, by means of a flange connection or the like. Located in the containment is the medium 2 to be measured.

Guided within the housing 3 is an immersion tube 4. A probe, not described in greater detail, is held within the immersion tube 4 by an accommodation likewise not described in greater detail. For example, the probe is connected with the immersion tube 4 by a screwed connection. The probe serves for determining one or more physical and/or chemical, process variables. Process variables that can be registered with the probe include, for example, pH-value, also as measured via ISFET, redox-potential, absorption of electromagnetic waves in the medium 2, for example, of wavelengths in the UV-, IR-, and/or visible region, oxygen, conductivity, turbidity, concentration of metal and/or non-metal materials and temperature.

The immersion tube 4 is axially displaceably held for movement along the central axis A in direction toward the containment, or away from the containment. Immersion tube 4 is, in such case, movable between the service position in the housing 3 and the process position outside of the housing 3. In the process position, measurement takes place, while in the service position the most varied of service tasks, such as cleaning or calibration, are performed. The shifting of the immersion tube 4 is effected through a manual or automatic, for example, pneumatic, hydraulic or electrical drive. Without limitation, a pneumatic drive is assumed in the following.

"Above" and related terms in the sense of this invention mean facing away from the medium 2, while "below" and related terms in the sense of this invention mean facing toward the medium 2.

Connected fixedly with the immersion tube 4 or being an integral part of the same is a piston 5. Piston 5 is in the form of a ring piston. Piston 5 divides the housing interior into an upper region 5.1 and a lower region 5.2. The immersion tube 4 can be moved via a first inlet 6 in the upper region 5.1 and a second inlet 7 in the lower region 5.2, respectively above and below the piston 5: If pressurized air is introduced into the upper region 5.1 through the first inlet 6, the immersion tube 4 moves in the direction of the medium 2, wherein simultaneously air from the lower region 5.2 flows out through the second inlet 7. Also, air can be actively sucked from the lower region 5.2, in order to support movement in the direction of the medium 2.

If pressurized air is introduced into the lower region 5.2 through the second inlet 7, the immersion tube 4 moves away from the medium 2, wherein simultaneously air flows from the upper region 5.1 out through the first inlet 6. Also, air can be actively sucked from the upper region 5.1, in order to support the movement.

Naturally, corresponding seals (not shown) assure that pressurized air does not escape and is only led through the inlets 6, 7.

Inlets 6, 7 are located laterally on the housing 3. The first inlet 6 can be located above the piston 5 (immersion tube 4 in the service position), while the second inlet 7 can be located below the piston 5 (immersion tube 4 in the process position). An option is that the two inlets 6, 7 on the housing 3 are located above or below the piston 5 (immersion tube 4 in the service position) and for the ability to function a line 20 is led in the interior of the housing 3 into the region 5.2 below the piston 5. Line 20 can also serve as a twist preventer for the immersion tube 4. Inlets 6, 7 need not necessarily lie in the same frontal plane.

FIG. 1 shows the situation shortly before the immersion tube reaches the process position. Shown, furthermore, is a first end position detent 8, which is composed at least of a blocking member 10 and a spring 11. Located on the lower end region of the immersion tube 4 is a first shifting element 9. Shifting element 9 is conically embodied, wherein the base of the cone is located on the immersion tube 4. There is formed, thus, an incline 9.1 tapering toward the central axis A. Incline 9.1 has a cone angle less than/equal to 45°. The shifting element 9 is implemented either as an integral part of the immersion tube 4 or as a conical screw.

If the shifting element 9, in the case of movement of the immersion tube 4 from service into process position, reaches the blocking member 10, then blocking member 10 is shifted via the incline 9.1 counter to the spring bias of spring 11 radially outwards. Upon additional movement such that shifting element 9 passes the blocking member 10, blocking member 10 is pressed by the spring 11 back into the rest position, where it engages in a groove 12 on the immersion tube 4. Groove 12 is embodied, for example, as an annular groove.

During the shifting of the immersion tube 4 from service into process position, pressurized air is also expelled by means of the piston 5 through the second inlet 7. Pressurized air is sufficient to shift the blocking member 10 against the spring bias of spring 11 and piston 5 can thus pass the blocking member 10 unimpeded. Thereupon, the blocking member 10 enters into engagement with the groove 12 provided therefor.

Figure 2:
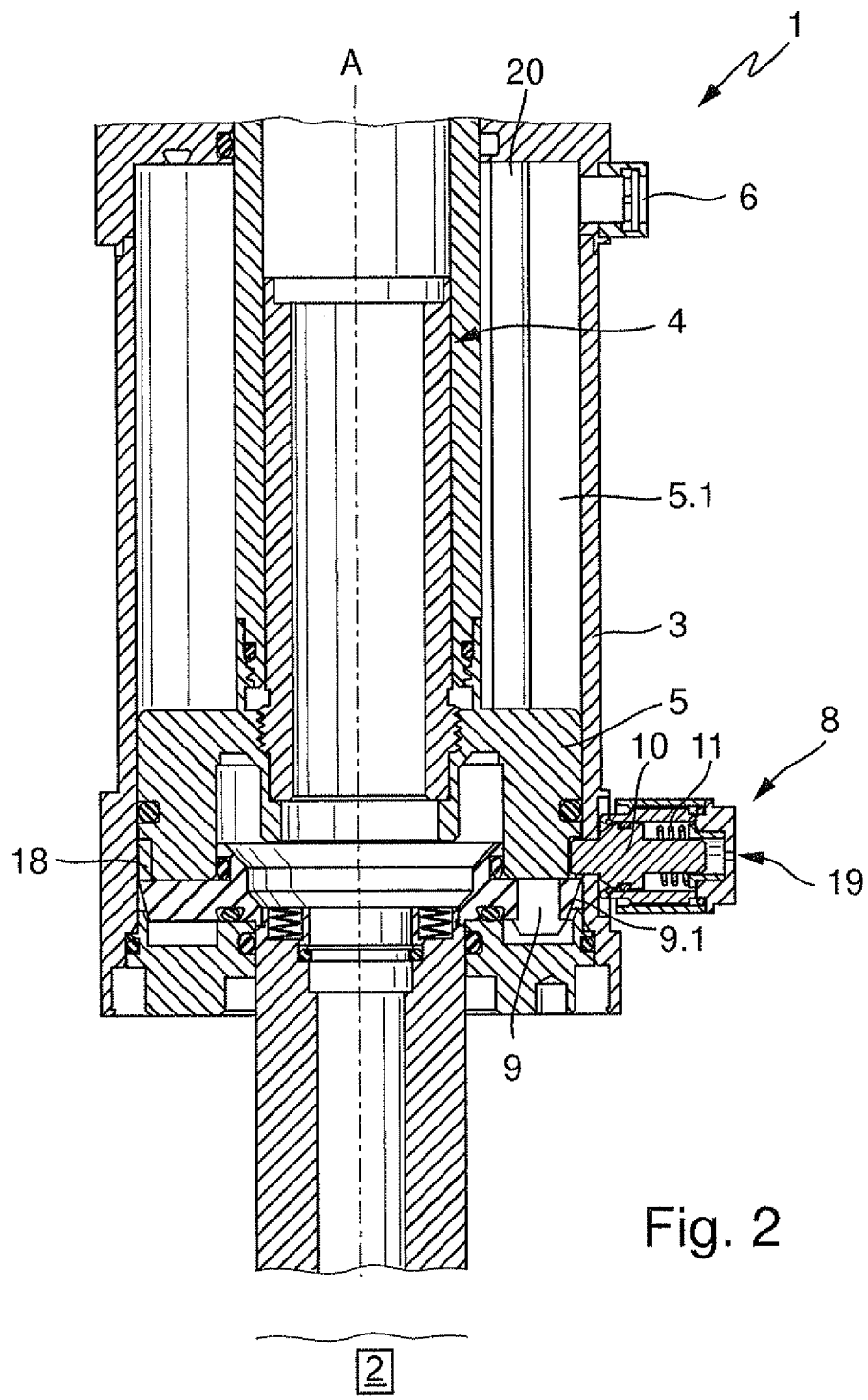
FIG. 2 a cross section of the retractable assembly of the invention in the process position.

If, now, the drive fails, only the force resulting from the process pressure acts on the immersion tube 4, so that the immersion tube 4 wants to shift upwardly. This is, however, prevented by the groove 12, since the end position detent 8 remains in the locked position, as shown in FIG. 2.

Only as pressure is increased in the lower region 5.2, first of all, the blocking member 10 is shifted radially outwards and then the piston 5 (including the immersion tube 4) is shifted upwardly. This becomes possible, because the inner resistances and the spring force 11 are so matched to one another that the force increasing in proportion to the pressure rise is first only sufficient to move the blocking member 10 and only after further increase to move the piston 5.

There are situations, e.g. cases of emergency, in which the immersion tube 4 must be released immediately from the locked position. Therefore, a first emergency unlock 19 is provided, which brings the blocking member 10 out of the groove 12 and so enables a movement of the immersion tube 4, even when no pressurized air is present.

Figure 3:
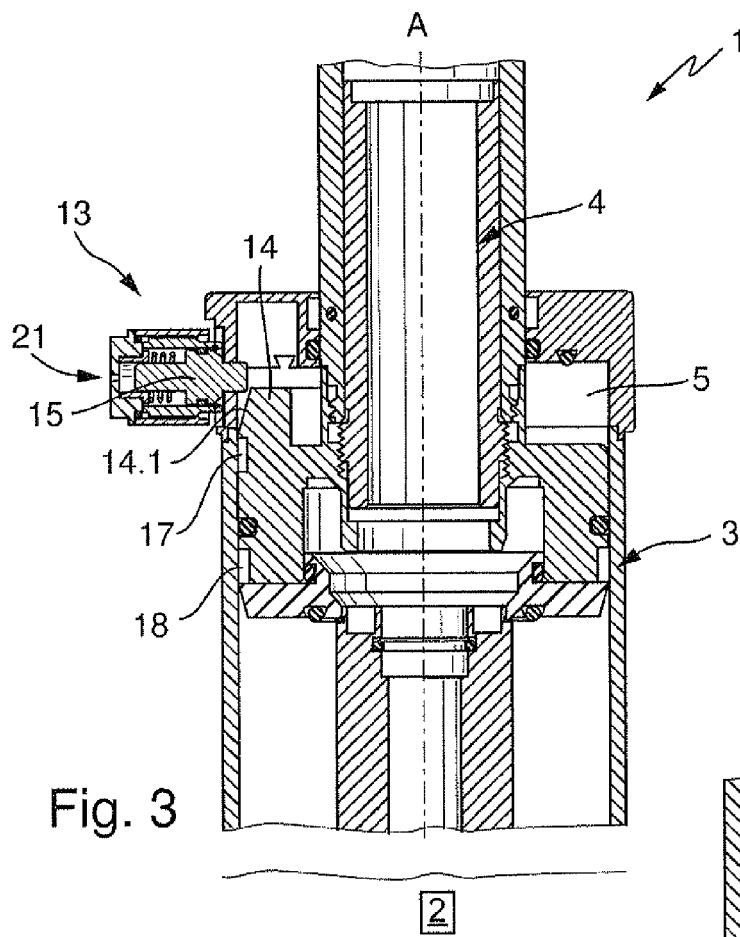
FIG. 3 a cross section of the retractable assembly of the invention shortly before the immersion tube reaches the service position.

FIG. 3 shows the situation shortly before the immersion tube reaches the service position. Shown is a second end position detent 13, which is composed at least of a blocking member 15 and a spring 16. Located on the upper end region of the immersion tube 4 is a second shifting element 14. Shifting element 14 includes an incline 14.1 tapering toward the central axis A. This incline 14.1 has a cone angle less than/equal to 45°. Shifting element 14 is either an integral part of the immersion tube 4 or implemented as a conical screw.

If the shifting element 14, in the case of movement of the immersion tube 4 from process—into service position, reaches the blocking member 15, then blocking member 15 is shifted by the incline 14.1 counter to the spring bias of spring 16 radially outwards. Upon further movement, the blocking member 15, after passing the shifting element 14, is pressed back by the spring 16 into the rest position, where it engages in a second groove 17 on the immersion tube 4. Groove 17 is embodied, for example, as a groove with the shape of a circular segment, as a radial bore or as a tangential cavity on the periphery of the immersion tube 4.

The shifting of the immersion tube 4 from service to process position also expels pressurized air by means of the piston 5 through the first inlet 6. This pressurized air is sufficient to shift the blocking member 15 against the bias of spring 16, so that the piston 5 can pass by the blocking member 15 unimpeded. Then, the blocking member 15 enters into engagement with the groove 17 provided therefor.

Figure 4:
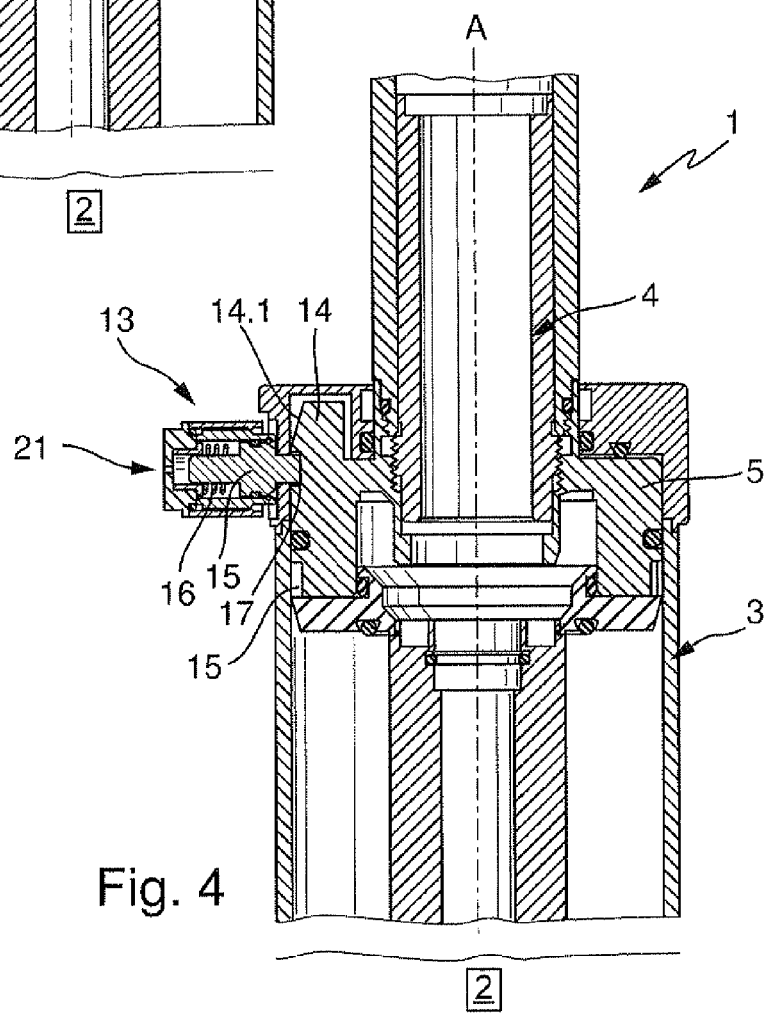
FIG. 4 a cross section of the retractable assembly of the invention in the service position.

If, now, the drive fails, the immersion tube 4 is, nevertheless, held in position, since the end position detent 13 remains in the locked position, as shown in FIG. 4.

Only when pressure in the upper region 5.1 is increased, first the blocking member 15 is shifted radially outwards and then the piston 5 (including the immersion tube 4) shifts downwards. This becomes possible, since the inner resistances and the spring force 16 are so matched to one another that force increasing in proportion to the pressure rise is first only sufficient to move the blocking member 15 and only after further rise then the piston 5.

There are situations, e.g. cases of emergency, in which the immersion tube 4 must be immediately freed from the locked position. Therefore, a second emergency unlock 21 is provided, which releases the blocking member 15 immediately from the groove 17 and so enables movement of the immersion tube 4 even when no pressurized air is present.

The inlets 6, 7 and the end position locks 8, 13 need not necessarily lie in a plane. Thus, the inlets are not visible in FIGS. 3 and 4.

The invention claimed is:

1. A retractable assembly for immersion-, flow- and appendage-measuring systems in analytical process technology for measuring at least one measured variable of a medium, comprising:
 a cylindrical housing;
 an immersion tube with a piston, wherein said immersion tube is axially movable between a service position run out from the medium and a process position run into the medium by means of a pressurized air, wherein at least a first inlet and a second inlet are provided on said cylindrical housing, wherein said first inlet is located on a side of said piston facing away from the medium and said second inlet is located on a side of said piston facing the medium, wherein the immersion tube is moved from the service position to the process position by supplying said first inlet with the pressured air, and wherein said immersion tube is moved from the process position to the service position by supplying said second inlet with the pressurized air;

at least a first end position detent secured to said cylindrical housing for holding said immersion tube in the process position;

a first shifting element provided, at an immersion tube end region facing the medium, which is so embodied that, in the case of moving of said immersion tube from the service position to the process position, and a first mechanical blocking member shifts essentially radially against a spring bias, wherein:

said first mechanical blocking member engages in a first groove on said immersion tube, whereby movability of said immersion tube is blocked;

said first groove is located in the movement direction from the service position to the process position behind said first mechanical blocking member; and said spring bias is so embodied that supplying of said second inlet with the pressurized air directly releases said first mechanical blocking member from the groove, whereby movement of said immersion tube from the process position to the service position becomes possible.

2. The retractable assembly as claimed in claim 1, wherein:
a second end position detent is provided secured to said housing for holding said immersion tube in the service position;

at an immersion tube end region facing away from the medium, a second shifting element is provided, which is so embodied that, in the case of moving of said immersion tube from the process position to the service position, a second mechanical blocking member shifts essentially radially against a spring bias, and said second mechanical blocking member engages in a second groove on said immersion tube, whereby movability of the immersion tube is blocked;

said second groove is located in the movement direction from the process position to the service position behind said second mechanical blocking member; and the spring bias is so embodied that supplying said first inlet with the pressurized air directly releases said second mechanical blocking member from said second groove, whereby movement of said immersion tube from the service position to the process position becomes possible.

3. The retractable assembly as claimed in claim 2, wherein:
at least one of said shifting elements is embodied conically; and
the base of the cone is located on said immersion tube.

4. The retractable assembly as claimed in claim 3, wherein:
at least one of said shifting elements is embodied as a frustum.

5. The retractable assembly as claimed in claim 4, wherein:
said frustum is embodied by a securement element with conical head.

6. The retractable assembly as claimed in claim 3, wherein:
the half cone angle of said cone shaped shifting element amounts to less than or equal to 45°.

7. The retractable assembly as claimed in claim 1, wherein:
at least one of said grooves is embodied as an annular groove.

8. The retractable assembly as claimed in claim 7, wherein:
a sliding ring is provided in said at least one groove for increasing movability of said immersion tube; and
a region of said sliding ring is omitted for said first and/or second mechanical blocking member.

9. The retractable assembly as claimed in claim 1, wherein:
at least one of said grooves is embodied as one of:
a circular segment shaped groove, a radial bore and as a tangential cavity on the periphery of the immersion tube.

10. The retractable assembly as claimed in claim 1, wherein:
at least one emergency unlock is provided, which releases said first and/or second mechanical blocking member from said first and/or second groove and so enables movement of said immersion tube even when no pressurized air is present.

11. A method for assuring in any situation that an immersion tube of a retractable assembly cannot move uncontrollably from a service or process position, comprising the steps of:
axially moving said immersion tube between a service position run out from the medium and a process position run into the medium by means of a pressurized air, wherein at least a first inlet and a second inlet are provided on a housing, wherein said first inlet is located on the side of a piston facing away from the medium and said second inlet is located on the side of the piston facing the medium, wherein the immersion tube is moved from the service position to the process position by supplying said first inlet with the pressurized air, and wherein said immersion tube is moved from the process position to the service position by supplying said second inlet with the pressurized air;

shifting a first shifting element through movement of the immersion tube from the service position to the process position;

engaging a first mechanical blocking member in the course of further movement of the immersion tube in a first groove on the immersion tube, and preventing further movement of the immersion tube;

holding said immersion tube in the process position with at least a first end position detent secured to the housing; and supplying intendedly said second inlet with the pressurized air for directly releasing said first mechanical blocking member from said first groove, and moving the immersion tube back from the process position to the service position.

12. Method as claimed in claim 11, further comprising the steps of:
shifting a second shifting element through movement of the immersion tube from the process position to the service position;

engaging a second mechanical blocking member in the course of further movement of the immersion tube in a second groove on the immersion tube, and preventing further movement of the immersion tube;

holding said immersion tube in the service position with a second end position detent secured to the housing; and supplying intendedly said first inlet with pressurized air for directly releasing said second mechanical blocking member from said second groove, and moving the immersion tube back from the service position to the process position.

* * * * *